(12) United States Patent
Devanathan

(10) Patent No.: US 6,749,426 B2
(45) Date of Patent: Jun. 15, 2004

(54) BONDABLE ORTHODONTIC APPLIANCE

(75) Inventor: Thrumal Devanathan, Westville, IN (US)

(73) Assignee: TP Orthodontics, Inc., Westville, IN (US)

( * ) Notice: Subject to any disclaimer, the term of this patent is extended or adjusted under 35 U.S.C. 154(b) by 176 days.

(21) Appl. No.: 09/969,475

(22) Filed: Oct. 2, 2001

(65) Prior Publication Data

US 2003/0064343 A1 Apr. 3, 2003

(51) Int. Cl.⁷ ................................................. A61C 3/00
(52) U.S. Cl. .......................................................... 433/9
(58) Field of Search ........................... 433/9, 8, 10, 11, 433/12, 13, 14, 15, 16, 17

(56) References Cited

U.S. PATENT DOCUMENTS

| 2,794,788 | A | * | 6/1957 | Coover et al. | 524/418 |
| 4,068,379 | A | | 1/1978 | Miller et al. | 433/9 |
| 4,337,037 | A | * | 6/1982 | Kurz | 43/8 |
| 4,826,430 | A | * | 5/1989 | Chen et al. | 433/8 |
| 4,948,367 | A | | 8/1990 | Haas | 433/9 |
| 5,110,290 | A | | 5/1992 | Wong | 433/9 |
| 5,232,361 | A | * | 8/1993 | Sachdeva et al. | 433/9 |
| 5,722,826 | A | | 3/1998 | Tuneberg et al. | 433/9 |
| 5,810,584 | A | | 9/1998 | Wong | 433/9 |

* cited by examiner

Primary Examiner—John J. Wilson
(74) Attorney, Agent, or Firm—Lloyd L. Zickert

(57) ABSTRACT

A bondable orthodontic appliance such as a molar tube bondable to a tooth by use of a light-cure adhesive for bond sites at the posterior of the mouth wherein the bonding pad of the appliance includes a light-cure adhesive bonding face.

4 Claims, 2 Drawing Sheets

BONDABLE ORTHODONTIC APPLIANCE

DESCRIPTION

This invention relates in general to a bondable orthodontic appliance, and more particularly to an appliance bondable to a tooth with a light-cure adhesive, and still more particularly to a bondable orthodontic appliance for the posterior teeth having a light-cure adhesive bonding face bondable to a tooth by a light-cure adhesive.

BACKGROUND OF THE INVENTION

Orthodontic treatment of a patient usually begins with the placement of fixed appliances, which includes molar tubes at the distal ends of the arches for receiving and anchoring distal ends of archwires. Such tubes are usually mounted with bands. Mounting tubes by bonding is becoming more popular.

Heretofore, it has been well known to bond appliances to teeth with lightcure adhesives, and that the advantage of directly bonding appliances to teeth permits a lower profile, thereby eliminating the need for offset bends in archwire. While it is known to bond molar tubes to molar teeth at the posterior of the mouth, it is also known that molar tubes require higher bond strengths because they are subjected to greater forces from the archwire during orthodontic treatment.

It is also known that bonding with light-cure adhesives requires good access to the bond site in order to allow the light source to properly penetrate and adequately cure the adhesive. Good access is not generally possible when mounting current bondable appliances to molar teeth. Inadequate curing of a light-cure adhesive results in premature separation of the appliance from a tooth, requiring rebonding during the treatment of a patient, which is not only time-consuming to the orthodontic practitioner but can adversely affect the treatment time when rebonding may be delayed.

When bonding an appliance to a tooth with a light-cure adhesive, one of the problems encountered in bonding molar appliances is in obtaining a satisfactory cure of the adhesive. Molars are far back in the mouth at the posterior of the arch, and while a curing light can easily direct light to the mesial and occlusal edges of a bonding pad, it is not possible to direct the light at the distal and gingival edges of the pad. Therefore, when mounting an appliance on a tooth, because adhesive must fill the spaces on the bonding face of an appliance which are not accessible to a light source at the mesial and distal edges of an appliance, incomplete curing results in producing an unreliable bond for maintaining the appliance in place throughout orthodontic treatment.

SUMMARY OF THE INVENTION

The present invention solves the bonding strength problem by providing a bondable appliance that enhances the curing of the light-cure adhesive at bonding sites deeper in the oral cavity in the posterior of the arches.

Bondable appliances include a bonding pad that is either integrally formed with the appliance by casting so it is one piece or is attachable to the appliance by a suitable method. For example, it is well known to provide mesh bonding pads consisting of a metal foil and mesh attached to the foil such as closed in U.S. Pat. No. 4,068,379. Such a mesh bonding pad is securable to an appliance such as by welding.

It is also well known, as shown in the above identified patent, to provide one-piece appliances that have a bonding pad integrally formed with the appliance and with a textured bonding face for receiving a bondable adhesive and for attachment to a tooth.

It is also known to cure light-cure adhesive in a bonding process by using a light-curing unit or a plasma arc light-curing unit, the latter of which significantly reduces the light-curing time over the conventional light-curing unit.

The present invention enhances the bond strength when bonding an appliance to a tooth by precoating the bondable surface of the appliance with a light-cure adhesive prior to bonding the appliance to a tooth with light-cure adhesive. More specifically, the heretofore encountered problem of incomplete curing of a light-cure adhesive when bonding a molar appliance is solved by applying a light-cure adhesive over the bonding pad of an appliance and then curing that adhesive when it can be fully subjected to a curing light at the factory. Thereafter, when the adhesive-filled pad of the appliance is to be mounted on a molar tooth, the entire light-curable adhesive added between the pad and tooth will be more accessible to a light-curing operation because the layer of adhesive provided between the cured adhesive surface of the molar pad and the tooth can be more fully subjected to the light-curing energy. Accordingly, a more reliable bond is obtained to enhance the bond strength.

The present invention also involves the steps of making the appliance with its light-cure adhesive pad prior to the application of the light-cure adhesive to the pad of the appliance during mounting of the appliance on a tooth so as to assure a strong bond between the adhesive and the bonding pad of the appliance.

Preparing the bondable appliance first requires thoroughly cleaning the appliance with a plasma cleaning machine. The bonding pad is then treated with silane and prime coated with a thin layer of modified acrylic copolymer. The silane is cured before the application of the prime coat. After curing the prime coat, the pad is filled with a light-cure adhesive that is light cured. Thereafter, the surface of the adhesive is mechanically etched or sandblasted to create a rough surface for enhancing the bonding with adhesive when bonding the appliance on a tooth.

The strength of a bond for an appliance according to the present invention is about 25% greater than the strength of a bond of prior known appliances.

It is therefore an object of the present invention to provide a new and improved bondable orthodontic appliance bondable with a light-cure adhesive to a tooth.

It is a further object of the present invention to provide a bondable orthodontic appliance particularly for a bond site deep in the oral cavity having enhanced bond strength wherein the bonding base or pad of the appliance is pre-coated with a light-cured adhesive that is cured and surface roughened.

A further object of the present invention is in the provision of a method of making a bonding base on an orthodontic appliance with a light-cure bonding material face including the steps of cleaning the appliance and bonding base, applying a coating of silane to the base, heat-curing the silane, applying a coating of acrylic copolymer to the base, and covering the base with a light-curable adhesive, and light-curing the adhesive.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figure 1:
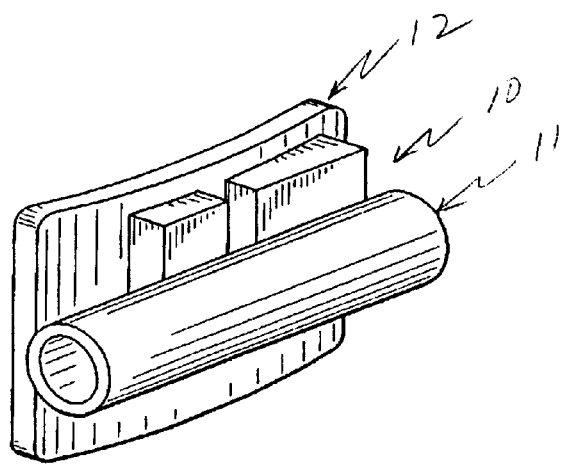
FIG. 1 is a front perspective view of a bondable molar tube according to the invention.

The present invention is in a bondable orthodontic appliance that when bonded to a tooth with a light-cure adhesive has enhanced bond strength as above mentioned. While it has been known for some time to attach orthodontic appliances to teeth by a bonding process, the direct bonding of molar tubes has not been as reliable because it is difficult to light-cure the adhesive on the bonding pad when mounting appliances at the posterior of the arch. Thus, the molar appliances have often been mounted on a tooth with the well known band technology in order to withstand forces encountered throughout the treatment of a patient. However, the added advantage of maintaining a lower profile with a bonded appliance to eliminate the need for offset bends in archwires often influences the orthodontic practitioner to resort to bonding molar tubes with light-cure adhesives.

The bondable appliance of the present invention is provided with a bonding pad or base prefilled and coated with a light-cure adhesive. Application of a light-cure adhesive to the pad and curing of the adhesive before proceeding to mount the appliance on a tooth provides a better cure and bonding of the adhesive engaging the pad or base of an appliance that thereafter can be better bonded to a tooth with a light-cure adhesive, resulting in obtaining enhanced bond strength. Thus, the higher bond strengths required for molar tubes that are located deeper in the oral cavity reduces the probability of bond failure during orthodontic treatment.

Referring to the drawings, a bondable molar tube 10 is shown that includes an appliance 11 in the form of a molar tube suitably attached to a base or pad 12. It will be appreciated that while the present invention is illustrated and described in connection with the use of an improved bondable pad for a molar tube, the bondable pad may be used on any other appliance for the mouth. For example, it could be used on brackets, hooks, headgear tubes, lip bumper tubes, or other appliances. It also will be understood that the bondable appliance of the invention is not limited to an appliance that is only suitable for use on posterior teeth.

The base or pad 12 of the bondable appliance 10 includes a metal foil 13 having a metal mesh section 14 suitably secured thereto. This mesh may be woven or otherwise constructed.

When constructing the base or pad of foil and wire mesh, the pad would normally be welded to the appliance 11 to therefore provide a combination appliance base or pad. As already above mentioned, it should be appreciated that the appliance could be formed by casting and include an integral pad. The appliance would then be a one-piece unit, and in that event the bondable surface of the pad would be formed with pockets or dimples to receive and lock in the adhesive when it is applied to the bonding face as the appliance is being manufactured.

Figure 2:
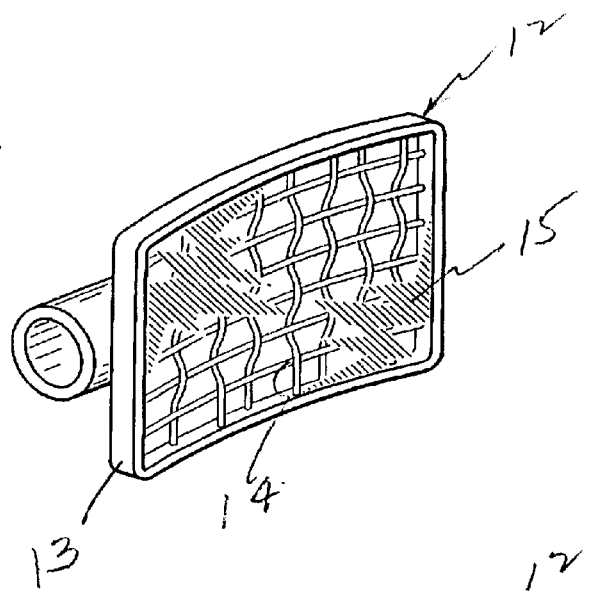
FIG. 2 is a rear perspective view of the tube of FIG. 1 and illustrating the cured adhesive bonding pad.
Figure 3:
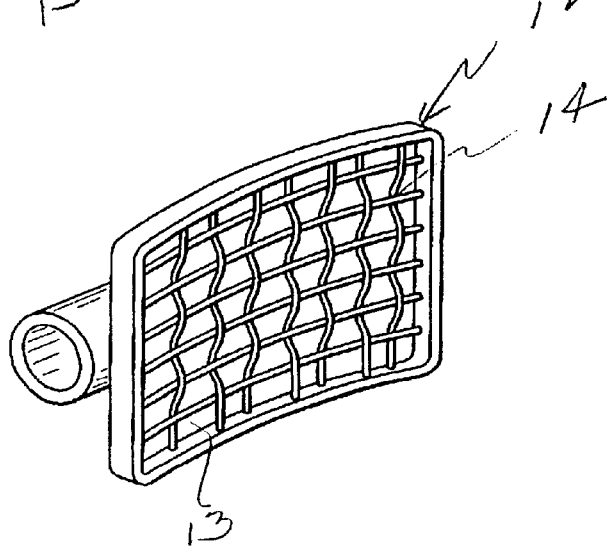
FIG. 3 is a perspective view like FIG. 2 but illustrating the bonding pad prior to the filling of the pad with a light-cure adhesive.

FIG. 3 shows the bonding pad 12 of the appliance prior to the application of light-cure adhesive and FIG. 2 shows the applied and cured light-cure adhesive as designated by the numeral 15, which then completely encapsulates the mesh 14 of the pad.

The appliance is provided with the light-cure adhesive 15 after it is suitably prepared so that the light-cure adhesive will be strongly, fully and completely held in place in the bonding pad. The appliance is supplied to the orthodontist in this form.

When making the appliance after the appliance has been either attached to a foil mesh pad or the appliance is cast as a unitary item, the appliance is thoroughly cleaned by the use of a suitable plasma cleaning machine. Such plasma cleaning machines are well known, such as the machine made by Advanced Plasma Systems, Inc. of Florida.

Following the cleaning of the appliance to remove all residue, the bondable surfaces including the mesh and foil, is silane treated. Any suitable silane may be used, such as a silane obtained from Aldrich Chemicals of Wisconsin. Once the mesh and foil is coated with silane, it is then suitably heat-cured. Thereafter, the base is prime coated with a thin layer of modified acrylic copolymer, such as the copolymer Vareloid available from Rohm & Haas in Pennsylvania. The copolymer is also then heat-cured.

Following the curing of the copolymer, the mesh and foil are then filled with a relatively thick light-cure adhesive that is suitably light-cured. This then presents a smooth surface as the adhesive is applied with a spatula to smooth it before curing. It will be appreciated that the adhesive will be thoroughly light-cured as a light source can be directly applied over the entire area where the adhesive is located to obtain a fully cured adhesive. The relatively smooth surface of the adhesive may be suitably further smoothed by any suitable means if desired. Then the surface is mechanically etched or sandblasted to create a rough surface. The roughened texture of the surface thereby enhances further bonding with adhesive.

Figure 4:
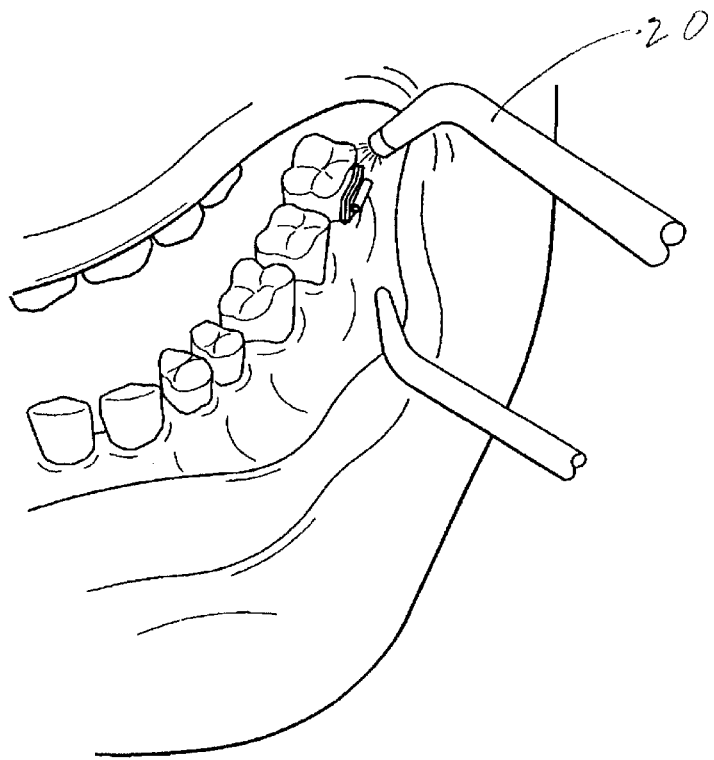
FIG. 4 is a fragmentary perspective view of the mouth of a person and illustrating the application of a curing light to a bondable molar tube on a molar deep in the oral cavity of a patient.
Figure 5:
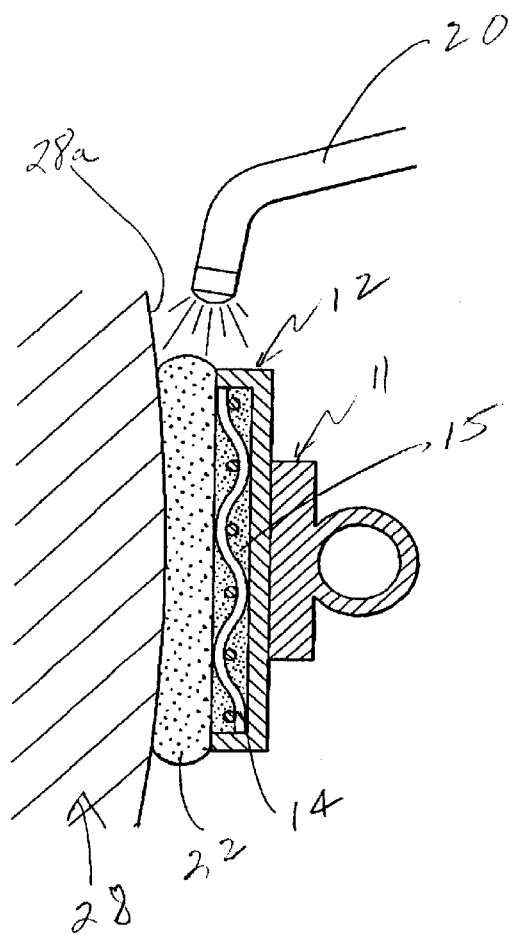
FIG. 5 is a greatly enlarged vertical sectional view taken through an appliance according to the invention and illustrating the application of light energy for curing of a light-cure adhesive applied between the appliance and a tooth, wherein the adhesive thickness between the appliance and the tooth is somewhat exaggerated to show the ability to have the light source penetrate fully through the adhesive during the curing step.

As seen in FIG. 4, the light-curing step involves holding a light probe 20 at the appliance as it is being mounted on a molar tooth. As also seen in FIG. 5, the layer of light-cure adhesive 22 is relatively uniformly sized and positioned between the face 15a of the light-cure adhesive 15 on the appliance and the face 28a on the tooth 28. Effectively, the adhesive layer 22 on the tooth can be entirely exposed to the energy of the light-cure probe 20 during the bonding of the appliance to the tooth. Because of the light-cure adhesive 15 on the appliance, the light-curable adhesive used to bond the appliance to the tooth does not flow into the cavities of the bonding pad, and therefore the light source is fully applied to the entire layer of the adhesive 22 that is employed to bond the appliance to the tooth. Thus, the bond strength of the appliance is enhanced.

It will be understood that modifications and variations may be effected without departing from the scope of the novel concepts of the present invention, but it is understood that this application is to be limited only by the scope of the appended claims.

The invention is hereby claimed as follows:

1. The method of factory-making a bonding base on an orthodontic appliance for delivery to a user with a light-cured bonding material face from a bonding base having a layer of metal mesh, the method comprising the steps of:

cleaning the appliance and bonding base by a plasma cleaning machine, applying a coating of silane to the mesh, heat-curing the silane, applying a coating of modified acrylic copolymer to the mesh, heat-curing said acrylic copolymer, and covering the mesh with a light-curable adhesive and light-curing the adhesive at the factory.

2. The method of claim 1, which includes the further step of roughening the surface of the cured adhesive.

3. The method of claim 2, wherein the step of roughening includes etching the surface.

4. The method of claim 2, wherein the step of roughening includes mechanically etching the surface.

* * * * *